(12) United States Patent
Mehrer

(10) Patent No.: US 7,297,734 B2
(45) Date of Patent: Nov. 20, 2007

(54) PROCESS FOR PREPARING SYNERGISTIC STABILIZER MIXTURES

(75) Inventor: Mathias Mehrer, Gablingen (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 0 days.

(21) Appl. No.: 10/504,118

(22) PCT Filed: Feb. 4, 2003

(86) PCT No.: PCT/IB03/00396

§ 371 (c)(1),
(2), (4) Date: Jun. 16, 2005

(87) PCT Pub. No.: WO03/066719

PCT Pub. Date: Aug. 14, 2003

(65) Prior Publication Data

US 2005/0228086 A1    Oct. 13, 2005

(30) Foreign Application Priority Data

Feb. 6, 2002 (DE) ............... 102 04 690

(51) Int. Cl.
*C08K 5/35* (2006.01)
*C09K 15/16* (2006.01)

(52) U.S. Cl. ............ 524/95; 252/401; 252/403; 528/367; 546/189

(58) Field of Classification Search ............ 252/401, 252/403; 524/95; 528/367; 546/189
See application file for complete search history.

(56) References Cited

U.S. PATENT DOCUMENTS

| | | | |
|---|---|---|---|
| 4,325,863 A | 4/1982 | Hinsken et al. |
| 4,338,244 A | 7/1982 | Hinsken et al. |
| 4,692,486 A | 9/1987 | Gugumus |
| 4,863,981 A | 9/1989 | Gugmus |
| 4,957,953 A | 9/1990 | Kikkawa et al. |
| 5,169,925 A | 12/1992 | Schmailzl et al. |
| 5,175,312 A | 12/1992 | Dubs et al. |
| 5,216,052 A | 6/1993 | Nesvadba et al. |
| 5,252,643 A | 10/1993 | Nesvadba et al. |
| 5,356,966 A | 10/1994 | Nesvadba et al. |
| 5,367,008 A | 11/1994 | Nesvadba et al. |
| 5,369,159 A | 11/1994 | Nesvadba et al. |
| 5,428,162 A | 6/1995 | Nesvadba et al. |
| 5,428,177 A | 6/1995 | Nesvadba et al. |
| 5,488,117 A | 1/1996 | Nesvadba et al. |
| 5,550,234 A | 8/1996 | Gaa et al. |
| 5,594,142 A | 1/1997 | Gaa et al. |
| 5,633,378 A | 5/1997 | Gaa et al. |
| 5,980,783 A | 11/1999 | Gugmus |
| 6,174,940 B1 | 1/2001 | Stahrfeldt et al. |
| 6,420,461 B1 | 7/2002 | Stahrfeldt et al. |

FOREIGN PATENT DOCUMENTS

| | | |
|---|---|---|
| DE | 4316611 | 11/1993 |
| DE | 4316622 | 11/1993 |
| DE | 4316876 | 11/1993 |
| EP | 449685 | 10/1991 |
| EP | 0589839 | 3/1994 |
| EP | 0591102 | 4/1994 |
| EP | 690060 | 1/1996 |
| EP | 705836 | 4/1996 |
| GB | 2267499 | 12/1993 |
| WO | WO 92/12201 | 7/1992 |
| WO | WO 94/22946 | 10/1994 |

OTHER PUBLICATIONS

PCT ISR for PCT/IB03/00396, Mar. 7, 2003.
PCT ISR for PCT/IB03/00396, Mar. 12, 2003.

*Primary Examiner*—Kriellion A Sanders
(74) *Attorney, Agent, or Firm*—Anthony A. Bisulca

(57) ABSTRACT

The present invention describes a process for preparing a synergistic stabilizer mixture comprising the components of the general formulae (I), (II) and (III) in accordance with claim 1, characterized by the reaction of compounds of the formula (V)

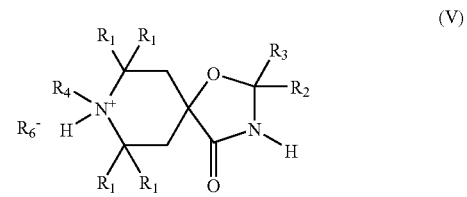

with an epihalohydrin of the formula (VI)

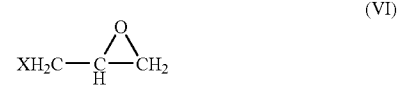

in the presence of a phase transfer catalyst and from 4 to 20 times the molar amount of an alkali metal hydroxide, relative to compound (V), at from 20 to 220° C. Removal of the excess epihalohydrin and phase separation are followed by polymerization at from 100 to 240° C.

31 Claims, No Drawings

PROCESS FOR PREPARING SYNERGISTIC STABILIZER MIXTURES

The invention relates to a process for preparing a synergistic stabilizer mixture based on polyalkyl-1-oxadiazaspirodecane compounds.

It is known that organic materials are damaged by light, radiation, heat or oxygen.

There are already numerous documents describing compounds for stabilizing organic materials against the effects of light and heat. Some of them relate to compounds based on 2,2,6,6-tetraalkylpiperidines. To afford effective protection, these stabilizers must be present at a sufficient concentration particularly at the exposed sites of the organic material.

The low molecular mass representatives of the 2,2,6,6-tetraalkylpiperidine class have the advantage of migrating rapidly to the sites that are especially subject to the damaging influences, where they unfold their protective effect. They have the dis-advantage, however, that their volatility is too high and they are readily extractable from the organic material.

The higher molecular mass representatives of this class, although not so readily extractable, have the disadvantage of being slower to migrate. Within the art this problem is often solved by employing a mixture of low (rapidly migrating) and high (slowly migrating) molecular mass stabilizers.

Accordingly, a considerable number of stabilizer mixtures based on sterically hindered amines are known from which the disadvantages depicted are largely or completely absent.

As representative examples mention may be made of mixtures as described, for example, in U.S. Pat. No. 4,692,486, U.S. Pat. No. 4,863,981, U.S. Pat. No. 4,957,953, U.S. Pat. No. 5,980,783, WO 92/12201, WO 94/22946, EP 449 685 A, EP 623 092 A, GB 2 267 499 A, and in *Research Disclosure* No. 34549 (January 1993).

There nevertheless continues to be a high demand for new, more powerful stabilizer mixtures which give organic materials enhanced light stability or service properties.

U.S. Pat. No. 6,174,940 describes a synergistic stabilizer mixture of the general formulae (I), (II) and (III) based on polyalkyl-1-oxadiazaspirodecane compounds, compound (I) being present in a fraction of 65-95%, preferably from 75 to 94%, in particular from 85 to 94% by weight, compound (II) in a fraction of from 5 to 35%, preferably from 5 to 20%, in particular from 5 to 12% by weight, and compound (III) in a fraction of from 0 to 10%, preferably from 1 to 5%, in particular from 1 to 3% by weight and in which
n and m independently of one another are a number from 0 to 100, but cannot both be 0,
$R^1$ is hydrogen, $C_5$-$C_7$ cycloalkyl or a $C_1$-$C_{12}$ alkyl group,
$R^2$ and $R^3$ independently of one another are a hydrogen atom, a $C_1$-$C_{18}$ alkyl group or, together with the carbon atom connecting them, a ring with a size of from 5 to 13 or, together with the carbon atom joining them, a group of the formula

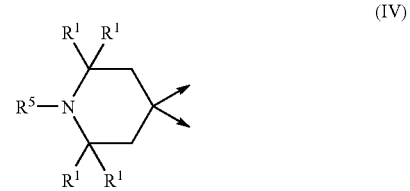

(IV)

$R^4$ and $R^5$ independently of one another are either hydrogen or a $C_1$-$C_{22}$ alkyl group, an oxygen radical O*, —OH, —NO, —CH$_2$CN, benzyl, allyl, a $C_1$-$C_{30}$ alkyloxy group, a $C_5$-$C_{12}$ cycloalkyloxy group, a $C_6$-$C_{10}$ aryloxy group, in which the aryl radical may also be substituted further, a $C_7$-$C_{20}$ arylalkyloxy group, in which the aryl radical may also be substituted further, a $C_3$-$C_{10}$ alkenyl group, a $C_3$-$C_6$ alkynyl group, a $C_1$-$C_{10}$ acyl group, halogen, or unsubstituted or $C_1$-$C_4$ alkyl-substituted phenyl.

The preparation of the individual components of the mixture has likewise already been described in U.S. Pat. No. 6,174,940, or references are made therein to the publications EP 705 836 A, EP 690 060 A and EP 057 885 A.

In U.S. Pat. No. 6,174,940, the mixture described is prepared by combining components (I), (II) and, where appropriate, (III) in the desired proportion.

This operation may take place, for example, in a powder mixer, in which the substances are mixed in dry form. Additionally or alternatively, the powder mixture can be homogenized by melting, under inert gas if necessary. The mixing operation may also be performed with the aid of a solvent, which after the components have been homogenized in solution is removed again by evaporation.

A procedure of this kind for preparing the mixture of components (I), (II) and (III) has the decisive disadvantage that it is time consuming, complex and costly, since each individual component must first of all be prepared independently and then, in a further, physical process operation, must be admixed in the correct, synergistic proportion.

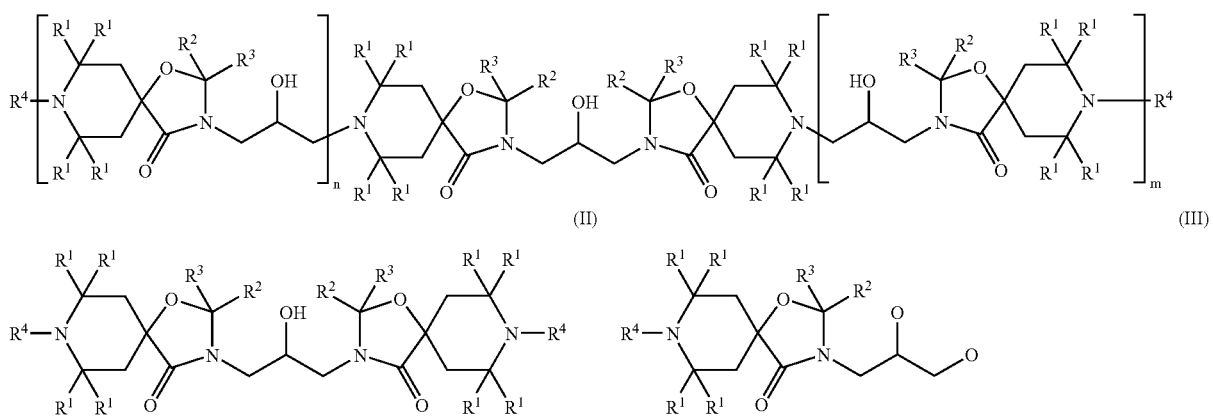

Surprisingly it has now been found that a mixture of components (I), (II) and (III) can be prepared by a skilful reaction regime in situ, i.e. without further physical process operations.

The invention accordingly provides a novel process for preparing a synergistic mixture comprising the components of the generate formulae (I), (II) and (III), the said mixture comprising compound (I) in a fraction of 65-95%, preferably from 75 to 94%, in particular from 85 to 94% by weight, compound (II) in a fraction of from 5 to 35%, preferably from 5 to 20%, in particular from 5 to 12% by weight, and compound (III) in a fraction of from 0 to 10%, preferably from 1 to 5%, in particular from 1 to 3% by weight,

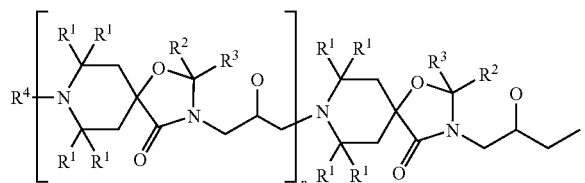

(I)

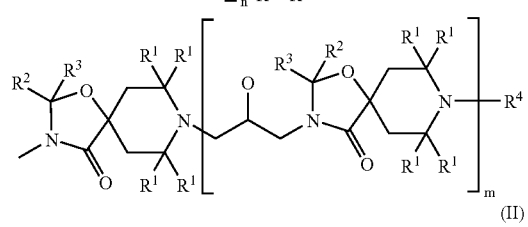

(II)

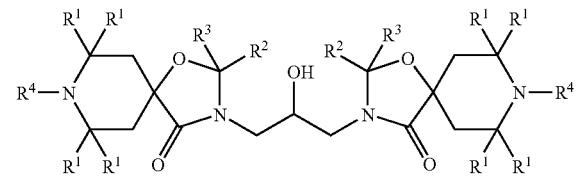

(III)

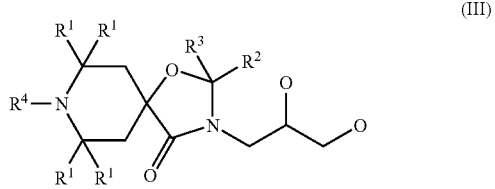

in which n and m independently of one another are a number from 0 to 100, but cannot both be 0, $R^1$ is hydrogen, $C_5$-$C_7$ cycloalkyl or a $C_1$-$C_{12}$ alkyl group, $R^2$ and $R^3$ independently of one another are a hydrogen atom, a $C_1$-$C_{18}$ alkyl group or, together with the carbon atom connecting them, a ring with a size of from 5 to 13 or, together with the carbon atom joining them, a group of the formula (IV),

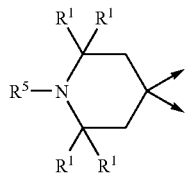

(IV)

and in which $R^4$ and $R^5$ independently of one another are either hydrogen or a $C_1$-$C_{22}$ alkyl group, an oxygen radical O*, —OH, —NO, —CH$_2$CN, benzyl, allyl, a $C_1$-$C_{30}$ alkyloxy group, a $C_5$-$C_{12}$ cycloalkyloxy group, a $C_6$-$C_{10}$ aryloxy group, in which the aryl radical may also be substituted further, a $C_7$-$C_{20}$ arylalkyloxy group, in which the aryl radical may also be substituted further, a $C_3$-$C_{10}$ alkenyl group, a $C_3$-$C_6$ alkynyl group, a $C_1$-$C_{10}$ acyl group, halogen, or unsubstituted or $C_1$-$C_4$ alkyl-substituted phenyl.

Preference is given to mixtures in which n and m independently of one another are a number from 0 to 10, but cannot both be 0, $R^1$ is hydrogen, $C_6$ cycloalkyl or a $C_1$-$C_4$ alkyl group, $R^2$ and $R^3$ independently of one another are a hydrogen atom or a $C_1$-$C_8$ alkyl group or together with the carbon atom connecting them, are a ring of size from 6 to 12, or, together with the carbon atom joining them, are a group of the formula (IV), $R^4$ and $R^5$ independently of one another are either hydrogen or a $C_1$-$C_5$ alkyl group, an oxygen radical O*, —OH, —NO, —CH$_2$CN, benzyl, allyl, a $C_1$-$C_{10}$ alkyloxy group, a $C_5$-$C_6$ cycloalkyloxy group, a $C_6$-$C_7$ aryloxy group, in which the aryl radical may also be substituted further, a $C_7$-$C_{10}$ arylalkyloxy group, in which the aryl radical may also be substituted further, a $C_3$-$C_6$ alkenyl group, a $C_3$-$C_6$ alkynyl group, a $C_1$-$C_4$ acyl group, halogen, or unsubstituted or $C_1$-$C_2$ alkyl-substituted phenyl.

Particular preference is given to mixtures in which n and m independently of one another are a number from 0 to 5, but cannot both be 0, $R^1$ is methyl, $R^2$ and $R^3$ together with the carbon atom connecting them are a ring of size 12 or, together with the carbon atom connecting them, are a group of the formula (IV) and $R^4$ and $R^5$ independently of one another are hydrogen, methyl, acetyl, octyloxy or cyclohexyloxy.

The synergistic mixture of components (I), (II) and (III) is prepared by reacting compounds of the general formula (V)

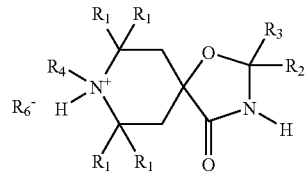

(V)

in which $R^1$, $R^2$, $R^3$ and $R^4$ are as defined above and $R_6^-$ is the anion of a protic acid of main group (V), (VI) or (VII) of the Periodic Table of the Elements (PTE), preferably from main group (VII) of the PTE, with an epihalohydrin of the formula (VI)

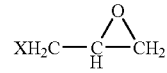

(VI)

in which X is a halogen atom, in particular a chlorine, bromine or iodine atom.

Anions of protic acids from main groups (V) and (VI) of the PTE are the anions of the oxoacids such as, for example, hydrogen sulphate, sulphate, nitrate, hydrogen phosphate and phosphate. Anions of the protic acids from main group (VII) of the PTE are, for example, fluoride, chloride, bromide and iodide. Particular preference is given to the chloride anion.

Compounds (V) and (VI) are premixed in a molar ratio of from 1:1 to 1:2.9 in the presence of a phase transfer catalyst in an inert organic solvent. The said premix is then reacted to form the desired synergistic mixture of components (I), (II) and (III), in the presence of from four to twenty times the molar amount of alkali metal hydroxide relative to the molar amount of the compounds of the formula (V), in an organic solvent using a phase transfer catalyst.

The alkali metal hydroxide can be used in solid form or else as an aqueous solution with a weight ratio of from 9:1 to 1:9 (parts of water to parts of alkali metal hydroxide).

Suitable compounds of the formula (V) are salts of a protic acid $HR_6^-$ with a compound selected from the around consisting of:
2-isopropyl-7,7,9,9-tetramethyl-1-oxa-3,8-diaza-4-oxospiro[4.5]decane,
2-butyl-7,7,9,9-tetramethyl-1-oxa-3,8-diaza-4-oxospiro[4.5]decane,
2-isobutyl-7,7,9,9-tetramethyl-1-oxa-3,8-diaza-4-oxospiro[4.5]decane,
2-pentyl-7,7,9,9-tetramethyl-1-oxa-3,8-diaza-4-oxospiro[4.5]decane,
2-hexyl-7,7,9,9-tetramethyl-1-oxa-3,8-diaza-4-oxospiro[4.5]decane,
2-heptyl-7,7,9,9-tetramethyl-1-oxa-3,8-diaza-4-oxospiro[4.5]decane,
2-isoheptyl-7,7,9,9-tetramethyl-1-oxa-3,8-diaza-4-oxospiro[4.5]decane,
2-isooctyl-7,7,9,9-tetramethyl-1-oxa-3,8-diaza-4-oxospiro[4.5]decane,
2-nonyl-7,7,9,9-tetramethyl-1-axa-3,8-diaza-4-oxospiro[4.5]decane,
2-isononyl-7,7,9,9-tetramethyl-1-oxa-3,8-diaza-4-oxospiro[4.5]decane,
2-undecyl-7,7,9,9-tetramethyl-1-oxa-3,8-diaza-4-oxospiro[4.5]decane,
2-phenyl-7,7,9,9-tetramethyl-1-oxa-3,8-diaza-4-oxospiro[4.5]decane,
2-(4-chlorophenyl)-7,7,9,9-tetramethyl-1-oxa-3,8-diaza-4-oxospiro[4.5]decane,
2,2-dimethyl-7,7,9,9-tetramethyl-1-oxa-3,8-diaza-4-oxospiro[4.5]decane,
2-ethyl-2,7,7,9,9-pentamethyl-1-oxa-3,8-diaza-4-oxospiro[4.5]decane,
2-propyl-2,7,7,9,9-pentamethyl-1-oxa-3,8-diaza-4-oxospiro[4.5]decane,
2-isopropyl-6,7,7,9,9-pentamethyl-1-oxa-3,8-diaza-4-oxospiro[4.5]decane,
2-butyl-2,7,7,9,9-pentamethyl-1-oxa-3,8-diaza-4-oxospiro[4.5]decane,
2-isobutyl-2,7,7,9,9-pentamethyl-1-oxa-3,8-diaza-4-oxospiro[4.5]decane,
2-pentyl-6,7,7,9,9-pentamethyl-1-oxa-3,8-diaza-4-oxospiro[4.5]decane,
2-hexyl-2,7,7,9,9-pentamethyl-1-oxa-3,8-diaza-4-oxospiro[4.5]decane,
2-nonyl-2,7,7,9,9-pentamethyl-1-oxa-3,8-diaza-4-oxospiro[4.5]decane,
2,2-diethyl-7,7,9,9-tetramethyl-1-oxa-3,8-diaza-4-oxospiro[4.5]decane,
2,2-dipropyl-7,7,9,9-tetramethyl-1-oxa-3,8-diaza-4-oxospiro[4.5]decane,
2,2-dibutyl-7,7,9,9-tetramethyl-1-oxa-3,8-diaza-4-oxospiro[4.5]decane,
2-ethyl-2-pentyl-7,7,9,9-tetramethyl-1-oxa-3,8-diaza-4-oxospiro[4.5]decane,
2,2-dibenzyl-7,7,9,9-tetramethyl-1-oxa-3,8-diaza-4-oxospiro[4.5]decane,
2,2,4,4-tetramethyl-7-oxa-3,12-diaza-14-oxodispiro[5.1.4.2]tetradecane,
2,2,4,4-tetramethyl-7-oxa-3,20-diaza-21-oxodispiro[5.1.11.2]heneicosane,
2,2,4,4-tetramethyl-7-oxa-3,14-diaza-15-oxodispiro[5.5.5.2]pentadecane,
2,2,4,4,10,10,12,12-octamethyl-7-oxa-3,11,14-triaza-15-oxodispiro[5.1.5.2]pentadecane,
2-ethyl-2,7,7,9,9-pentamethyl-1-oxa-3,8-diaza-4-oxo-8-oxylspiro[4.5]decane;
with the anion $R_6^-$ being, as defined above, an anion from a protic acid from main group (V), (VI) or (VII) of the PTE, preferably from main group (VII) of the PTE, and with particular preference chloride.

The polyalkyloxadiazaspirodecanes used as starting products are known in principle and are obtainable in accordance with the instructions given in U.S. Pat. No. 4,110,334 and U.S. Pat. No. 4,107,139.

Particularly preferred among the compounds (V) is 2,2,4,4-tetramethyl-7-oxa-3,20-diaza-21-oxodispiro[5.1.11.2]heneicosane hydrochloride.

A preferred epihalohydrin of the formula (VI) is epichlorohydrin.

Compounds of the formulae (V) and (VI) are reacted in a molar ratio of from 1:1 to 1:2.9; preferably from 1:1 to 1:2.7 and in particular from 1:2 to 1:2.5.

The reaction takes place in an inert organic solvent in the presence of from four to twenty times the molar amount of alkali metal hydroxide relative to compounds of the formula (V), in the form of solid alkali metal hydroxide, or of the corresponding amount of an aqueous alkali metal hydroxide solution, with a weight ratio of from 1:9 to 9:1, preferably from 2:3 to 4:1, and in particular from 1:1 to 7:3 (parts of alkali metal hydroxide to parts of water).

The reaction temperature lies in the range from 20 to 220° C., preferably from 40 to 120° C. and in particular from 60 to 90° C.

Preferred inert organic solvents are aliphatic or aromatic hydrocarbons, such as petroleum ether, hexane, heptane, petroleum fractions, toluene, cyclohexane, mesitylene or xylene, for example. Particular preference is given to aromatic hydrocarbons, especially xylene.

The inert organic solvent is preferably used in a weight ratio of from 2:1 to 1:5, more preferably from 2:1 to 1:3 and in particular from 2:1 to 1:2, relative to the compound (VI).

Phase transfer catalysts used are polyethylene glycols, preferably polyethylene glycols with an average degree of oligomerization, and in particular polyethylene glycol 200, in a quantitative proportion of from 1.5 to 10% by weight, preferably from 3 to 7% by weight and in particular 4-6% by weight, relative to the amount of the compound of the formula (V) used.

The reaction is generally over after from 30 to 60 minutes.

Following the reaction the excess of the epihalohydrin is removed from the reaction mixture, preferably by distillation. During the removal of the epihalohydrin, some or all of the inert organic solvent may be removed as well, and in that case must be made up in the appropriate amount before phase separation.

The organic and aqueous phases are separated; the organic phase is washed with water and the inert organic solvent is removed, preferably by distillation.

The viscose premix obtained can be converted without a further purification step, by heating at from 100 to 240° C., preferably from 120 to 220° C. and in particular from 150 to 200° C., preferably under reduced pressure, into the desired mixture of the formulae (I), (II) and (III).

By varying the amounts of the compounds of the formula (V) used, the amount of epihalohydrin (VI), the amount of alkali metal hydroxide used and the amount of polyethylene glycol phase transfer catalyst employed, it is possible to vary widely the composition of the mixture of components (I), (II) and (III).

The composition of the mixture (components (I), (II) and (III)) can be shown by conventional spectroscopic methods (IR and $^{13}$C-NMR spectroscopy).

Following polymerization, the reaction mixture may optionally be derivatized at the $R^4$ positions by known methods.

The mixtures of the formulae (I), (II) and (III) prepared by the process of the invention are suitable for use as light stabilizers in organic materials, as set out by way of example below.

1. Polymers of monoolefins and diolefins, for example polypropylene, polyisobutylene, polybutylene, polybut-1-ene, poly-4-methylpent-1-ene, polyisoprene or polybutadiene, and also polymers of cycloolefins, for example of cyclopentene or norbornene; additionally polyethylene (which optionally can be crosslinked); for example, high density polyethylene (HDPE), polyethylene of high density and high molar mass (HDPE-HMW), polyethylene of high density and ultrahigh molar mass (HDPE-UHMW), medium density polyethylene (MDPE), low density polyethylene (LDPE), linear low density polyethylene (LLDPE), branched low density polyethylene (BLDPE).

Polyolefins, i.e. polymers of monoolefins as exemplified in the preceding paragraph, in particular polyethylene and polypropylene, can be prepared by various, and especially by the following, methods:

a) free-radical polymerization (normally under high pressure and at elevated temperature)

b) catalytic polymerization using a catalyst that normally contains one or more metals of group IVb, Vb, VIb or VIII. These metals usually have one or more ligands, such as oxides, halides, alcoholates, esters, ethers, amines, alkyls, alkenyls and/or aryls that may be either π- or σ-coordinated. These metal complexes may be in the free form or fixed on substrates, for example on activated magnesium chloride, titanium(III) chloride, alumina or silicon oxide. These catalysts may be soluble or insoluble in the polymerization medium. The catalysts can be active as such in the polymerization or further activators may be used, for example metal alkyls, metal hydrides, metal alkyl halides, metal alkyl oxides or metal alkyloxanes, the metals being elements of groups Ia, IIa and/or IIIa of the Periodic Table. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polyethylene with polyisobutylene, polypropylene with polyethylene (for example PP/PE-HD/PE-LD) and mixtures of different types of polyethylene (for example PE-LD/PE-HD) with one another.

3. Copolymers of monoolefins and diolefins with each other or with other vinyl monomers, for example ethylene-propylene copolymers, linear low density polyethylene (PE-LLD) and mixtures thereof with low density polyethylene (PE-LD), propylene-but-1-ene copolymers, propylene-isobutylene copolymers, ethylene-but-1-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide, or ethylene-acrylic acid copolymers and their salts (ionomers), and also terpolymers of ethylene with propylene and a diene such as hexadiene, dicyclopentadiene or ethylidene-norbornene; and mixtures of such copolymers with one another and with polymers mentioned under 1), for example polypropylene-ethylene-propylene copolymers, PE-LD-ethylene-vinyl acetate copolymers, PE-LD-ethylene-acrylic acid copolymers, PE-LLD-ethylene-vinyl acetate copolymers, PE-LLD-ethylene-acrylic acid copolymers and alternating or random polyalkylene-carbon monoxide copolymers and mixtures thereof with other polymers, for example polyamides.

4. Hydrocarbon resins (for example $C_5$-$C_9$) including hydrogenated modifications thereof (e.g. tackifier resins) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methacrylate; mixtures of high impact strength of styrene copolymers and another polymer, for example a polyacrylate, a diene polymer or an ethylene-propylene-diene terpolymer; and block copolymers of styrene, such as styrene-butadiene-styrene, styrene-isoprene-styrene, styrene-ethylene/butylene-styrene or styrene-ethylene/propylene-styrene.

7. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, as well as mixtures thereof with the copolymers mentioned under 6), for example the copolymer mixtures known as ABS, MBS, ASA or AES polymers.

8. Halogen-containing polymers, such as polychloroprene, chlorinated rubber, chlorinated and brominated copolymer of isobutylene-isoprene (halobutyl rubber), chlorinated or sulphochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; as well as copolymers thereof such as vinyl chloride-vinylidene chloride, vinyl chloride-vinyl acetate or vinylidene chloride-vinyl acetate.

9. Polymers derived from α,β-unsaturated acids and derivatives thereof, such as polyacrylates and polymethacrylates, polyacrylonitriles, polyacrylamides and polymethyl methacrylates impact-modified with butyl acrylates.

10. Copolymers of the monomers mentioned under 9) with each other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallyl melamine; and also their copolymers with olefins mentioned in section 1.

12. Homopolymers and copolymers of cyclic ethers, such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulphides, and mixtures thereof with styrene polymers or polyamides.

15. Polyurethanes derived from hydroxyl-terminated polyethers, polyesters and polybutadienes on the one hand and aliphatic or aromatic polyisocyanates on the other, and also precursors thereof.

16. Polyamides and copolyamides derived from diamines and dicarboxylic acids and/or from aminocarboxylic acids or the corresponding lactams, such as polyamide 4, 6, 6/6, 6/10, 6/9, 6/12, 4/6, 12/12, 11 and 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide. Block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol. Additionally, polyamides or copolyamides modified with EPDM or ABS; and polyamides condensed during processing (RIM polyamide systems).

17. Polyureas, polyimides, polyamide-imides, polyether imides, polyester amides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether-esters derived from hydroxyl-terminated polyethers; and also polyesters modified with polycarbonates or MBS.

19. Polycarbonates and polyester carbonates.

20. Polysulphones, polyether sulphones and polyether ketones.

21. Crosslinked polymers derived from aldehydes on the one hand and phenols, urea or melamine on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example from epoxy acrylates, urethane acrylates or polyester acrylates.

25. Alkyd resins, polyester resins and acrylic resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, examples being products of bisphenol A diglycidyl ethers, bisphenol F diglycidyl ethers, which are crosslinked by means of customary hardeners, such as anhydrides or amines, for example, with or without accelerators.

27. Natural polymers such as cellulose, natural rubber, gelatin and derivatives thereof which have been chemically modified in a polymer-homologous manner, for example cellulose acetates, cellulose propionates and cellulose butyrates, or the cellulose ethers such as methyl cellulose; and also rosins and derivatives.

28. Mixtures (polyblends) of the aforementioned polymers, for example PP/EPDM, polyamide/EPDM or ABS, PVC/EVA, PVC/ABS, PVC/MBS, PC/ABS, PBTP/ABS, PC/ASA, PC/BT, PVC/CPE, PVC/acrylates, POM/thermoplastic PUR, PC/thermoplastic PUR, POM/acrylate, POM/MBS, PPO/MBS, PPO/HIPS, PPO/PA 6.6 and copolymers, PA/PE-HD, PA/PP, PA/PPO, PBT/PC/ABS or PBT/PET/PC.

29. Natural and synthetic organic substances which constitute pure monomeric compounds or mixtures thereof, examples being mineral oils, animal or vegetable fats, oils and waxes, or oils, waxes and fats based on synthetic esters (e.g. phthalates, adipates, phosphates or trimellitates), and also blends of synthetic esters with mineral oils in any desired proportion by weight, as are employed, for example, as spin finishes, and aqueous emulsions thereof.

30. Aqueous emulsions of natural or synthetic rubbers, such as natural rubber latex or latices of carboxylated styrene-butadiene copolymers.

The mixture of the formulae (I), (II) and (III) prepared by the process of the invention is used directly to stabilize the above organic materials or else in the form of a suitable combination with other additives, examples being antioxidants, light stabilizers, metal deactivators, antistatic agents, flame retardants, lubricants, nucleating agents, acid scavengers (basic costabilizers), pigments and fillers.

Antioxidants and light stabilizers which are used additionally to the compounds of the inventively prepared mixture (I), (III) and (III) are for example compounds based on sterically hindered amines or sterically hindered phenols or costabilizers containing sulphur or phosphor. Examples of suitable additives which can be employed in combination are as set out below:

1. Antioxidants 1.1 Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butyl-phenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or side chain-branched nonylphenols, such as 2,6-dinonyl-4-methylphenol, 2,4-dimethyl-6-(1'-methylundec- 1'-yl)phenol, 2,4-dimethyl-6-(1'-methylheptadec-1'-yl) phenol, 2,4-dimethyl-6-(1'-methyltridec-1'-yl)phenol and mixtures thereof 1.2 Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3 Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4 Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulphide.

1.5 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl) butane, 2,2-bis(3,5-di-tert-butyl-4-hydroxyphenyl) propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane, ethylene glycol bis[3,3-bis(3'-tert-butyl-4'-hydroxyphenyl)butyrate].

1.6 O-, N- and S-benzyl compounds, for example 3,5,3',5'-tetra-tert-butyl-4,4'-di-hydroxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulphide, isooctyl 3,5-di-tert-butyl-4-hydroxybenzylmercaptoacetate, tridecyl 4-hydroxy-3,5-di-tert-butylbenzylmercaptoacetate.

1.7 Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methyl-benzyl)malonate, didodecyl mercaptoethyl-2,2-bis(3,5-di-tert-butyl-4-hydroxybenzyl)malonate, di-[4-(1,1,3,3-tetramethylbutyl)phenyl]2,2-bis(3,5-di-tert-butyl-4-hydroxybenzyl)malonate.

1.8 Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)-phenol.

1.9 Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-tert-butyl-4-hydroxybenzyl)-isocyanurate, 1,3,5-tris(4-tert-butyl-3-hydroxy-2,6-dimethylbenzyl)-isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris-(3,5-dicyclohexyl-4-hydroxybenzyl) isocyanurate.

1.10 Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the Ca salt of the monoethyl ester of 3,5-di-tert-butyl-4-hydroxybenzylphosphonic acid.

1.11 Acylaminophenols, for example 4-hydroxylauranilide, 4-hydroxystearanilide, octyl N-(3,5-di-tert-butyl-4-hydroxyphenyl)carbamate.

1.12 Esters of β-(3,5-di-tert-butyl-4-hydroxyphenyl)propionic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13 Esters of β-(5-tert-butyl-4-hydroxy-3-methylphenyl) propionic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)propionic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenylacetic acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris-(hydroxyethyl)isocyanurate, N,N'-bis-(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,3-bis(3'-tert-butyl-4'-hydroxyphenyl)butyric acid with mono- or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-tert-butyl-4-hydroxyphenyl)propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

1.18 Tocopherol, such as, α-tocopherol, β-tocopherol, γ-tocopherol, δ-tocopherol and mixtures thereof (vitamin E).

1.19 Hydroxybenzyl aromatic, such as, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetra-methylbenzene, 2,4,6-tris(3,5-di-tert-butyl-4-hydroxybenzyl)phenol.

1.20 Ascorbic acid (vitamin C).

1.21 Amine antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(naphthyl-2-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphonamido)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methylphenyl)-amino]ethane, 1,2-di-(phenylamino)propane, (o-tolyl)biguanide, di[4-(1',3'-di-methylbutyl)-phenyl]amine, tert-octylated N-phenyl-1-naphthylamine, mixture of mono- and dialkylated tert-butyl/tert-octyldiphenylamines, mixture of mono- and dialkylated nonyldiphenylamines, mixture of mono- and dialkylated dodecyldiphenylamines, mixture of mono- and dialkylated isopropyl/isohexyl-diphenylamines, mixture of mono- and dialkylated tert-butyldiphenylamines, 2,3-dihydro-3,3-dimethyl-4H-1,4-benzothiazine, phenothiazine, mixture of mono- and dialkylated tert-butyl/tert-octyl-phenothiazines, mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl)sebacate, 2,2,6,6-tetramethylpiperidin-4-one, 2,2,6,6-tetramethylpiperidin-4-ol.

2. UV Absorbers and Light Stabilizers 2.1 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-[2'-hydroxy-5'-(1,1,3,3-tetramethylbutyl)phenyl]benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzo 2,2'-methylenebis[4-(1,1,3,3-tetramethylbutyl)-6-benzotriazol-2-ylphenol]; the transesterification product of 2-[3'-tert.butyl-5'-(2-methoxycarbonylethyl)-2'-hydroxyphenyl]benzotriazole with polyethylene glycol 300; [R—CH$_2$CH$_2$—COO (CH$_2$)$_3$]—$_2$ where R=3'-tert-butyl-4'-hydroxy-5'-2H-benzotriazol-2-ylphenyl.

2.2 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3 Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4 Acrylates, for example ethyl or isooctyl α-cyano-β,β-diphenylacrylate, methyl α-carbomethoxycinnamate, methyl or butyl α-cyano-β-methyl-p-methoxycinnamate, methyl, α-carbomethoxy-p-methoxycinnamate, N-(β-carbomethoxy-β-cyanovinyl)-2-methylindoline.

2.5 Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6 Sterically hindered amines, for example bis(2,2,6,6-tetramethylpiperidin-4-yl) sebacate, bis(2,2,6,6-tetramethylpiperidin-4-yl)glutarate, bis(2,2,6,6-tetramethylpiperidin-4-yl)succinate, bis(1,2,2,6,6-pentamethylpiperidin-4-yl)sebacate, bis-(1,2,2,6,6-pentamethylpiperidin-4-yl) glutarate, n-butyl-3,5-di-tert-butyl-4-hydroxybenzylmaleic acid-bis-(1,2,2,6,6-pentamethyl-piperidyl)-ester, 2,2,6,6-tetramethylpiperidyl behenate, 1,2,2,6,6-pentamethylpiperidyl behenate, the condensate of 1-hydroxyethyl-2,2,6,6-tetramethyl-4-hydroxypiperidine and succinic acid, the condensate of N,N'-bis-(2,2,6,6-tetramethyl-4-piperidyl)hexamethylendiamine and 4-tertoctylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butantetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, 4-stearoyloxy-2,2,6,6-tetramethylpiperidine, 4-stearyloxy-1,2,2,6,6-pentamethylpiperidine, 4-stearoyloxy-1,2,2,6,6-pentamethylpiperidine, bis-(1,2,2,6,6-pentamethylpiperidyl)2-n-butyl-2-(2-hydroxy-3,5-di-tert-butylbenzyl)-malonate, bis(1,2,2,6,6-pentamethylpiperidyl)2-n-butyl-2-(4-hydroxy-3,5-di-tertbutylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl)succinate, the condensate of N,N'-bis(2,2,6,6-tetramethyl-4-piperidyl)hexamethylenediamine and 4-morpholino-2,6-dichloro-1,3,5-triazine, the condensate of N,N'-bis(2,2,6,6-tetramethyl-4-piperidyl)hexamethylenediamine and 4-cyclohexylamino-2,6-dichloro-1,3,5-triazine, the condensate of 2-chloro-4,6-di-(4-n-butylamino-2,2,6,6-tetramethylpiperidyl)-1,3,5-triazine and 1,2-bis(3-aminopropylamino)ethane, the condensate of 2-chloro-4,6-di-(4-methoxypropylamino-2,2,6,6-tetramethylpiperidyl)-1,3,5-triazine and 1,2-bis(3-aminopropylamino)ethane, the condensate of 2-chloro-4,6-di-(4-methoxypropylamino-1,2,2,6,6-pentamethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, reaction products of 2-chloro-4,6-di-(4-n-butylamino-2,2,6,6-tetramethylpiperidyl)-1,3,5-triazine with mono- or polyfunctional amines, where between one and all the active hydrogen atoms on the amine are replaced, such as with ethylenediamine, diethylenetriamine, triethylenetetramine, hexamethylenediamine, 1,2-bis(3-aminopropylamino)ethane, reaction products of 2-chloro-4,6-di-(4-n-butylamino-1,2,2,6,6-penta-methylpiperidyl)-1,3,5-triazine with mono- or polyfunctional amines, where between one and all the active hydrogen atoms on the amine are replaced, such as with ethylenediamine, diethylenetriamine, triethylenetetramine, hexamethylenediamine, 1,2-bis(3-aminopropylamino)ethane, reaction products of 2-chloro-4,6-di-(4-n-butylamino-2,2,6,6-tetramethylpiperidyl)-1,3,5-triazine and 4-tert-octylamino-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis(3-aminopropylamino)ethane, reaction products of 2-chloro-4,6-di-(4-n-butylamino-1,2,2,6,6-pentamethylpiperidyl)-1,3,5-triazine and 4-tert-octylamino-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis(3-aminopropylamino)ethane, reaction products of 2-chloro-4,6-di-(4-n-butylamino-2,2,6,6-tetramethylpiperidyl)-1,3,5-triazine and 4-(4-n-butylamino-2,2,6,6-tetramethylpiperidyl)-2,6-dichloro-1,3,5-s-triazine with mono- or polyfunctional amines, where between one and all the active hydrogen atoms on the amine are replaced, such as with ethylenediamine, diethylenetriamine, triethylenetetramine, hexamethylenediamine, 1,2-bis(3-aminopropylamino)ethane, the condensate of 1,2-bis(3-aminopropylamino)ethane and 2,4,6-trichloro-1,3,5-triazine and also 4-butylamino-2,2,6,6-tetramethylpiperidine, N-(2,2,6,6-tetramethyl-4-piperidyl)-n-dodecylsuccinimide, N-(1,2,2,6,6-pentamethyl-4-piperidyl)-n-dodecylsuccinimide, 8-acetyl-3-dodecyl-7,7,9,9-tetramethyl-1,3,8-triazaspiro[4.5]decane-2,4-dione, oli-gomerized 2,2,4,4-tetramethyl-20-(oxiranylmethyl)-7-oxa-3,20-diaza-dispiro[5.1.11.2]heneicosan-21-one, oli-gomerized 1,2,2,4,4-pentamethyl-20-(oxiranylmethyl)-7-oxa-3,20-diazadispiro-[5.1.11.2]heneicosan-21-one, oli-gomerized 1-acetyl-2,2,4,4-tetramethyl-20-(oxiranylmethyl)-7-oxa-3,20-diaza-dispiro[5.1.11.2]heneicosan-21-one, 3-dodecyl-1-(2,2,6,6-tetramethyl-4-piperidyl)pyrrolidine-2,5-dione, 3-dodecyl-1-(1,2,2,6,6-pentamethyl-4-piperidyl)-pyrrolidine-2,5-dione, 2,2,4,4-tetramethyl-7-oxa-3,20-diazadispiro[5.1.11.2]heneicosan-21-one, 2,2,4,4-tetramethyl-7-oxa-21-oxo-3,20-diazadispiro[5.1.11.2]heneicosane-3-pro-panoic acid dodecyl ester, 2,2,4,4-tetramethyl-7-oxa-21-oxo-3,20-diazadispiro[5.1.11.2]heneicosane-3-pro-panoic acid tetradecyl ester, 2,2,3,4,4-pentamethyl-7-oxa-3,20-diazadispiro-[5.1.11.2]heneicosan-21-one, 2,2,3,4,4-pentamethyl-7-oxa-21-oxo-3,20-diaza-dispiro[5.1.11.2]heneicosane-3-propanoic acid dodecyl ester, 2,2,3,4,4-pentamethyl-7-oxa-21-oxo-3,20-diaza-dispiro[5.1.11.2]-heneicosane-3-propanoic acid tetradecyl ester, 3-acetyl-2,2,4,4-tetramethyl-7-oxa-3,20-diazadispiro[5.1.11.2]-heneicosan-21-one, 3-acetyl-2,2,4,4-tetramethyl-7-oxa-21-oxo-3,20-diaza-dispiro[5.1.11.2]heneicosane-3-propanoic acid dodecyl ester, 3-acetyl-2,2,4,4-tetramethyl-7-oxa-21-oxo-3,20-diaza-dispiro[5.1.11.2]heneicosane-3-propanoic acid tetradecyl ester, 1,1',3,3',5,5'-hexahydro-2,2',4,4',6,6'-hexaaza-2,2',6,6'-bismethano-7,8-dioxo-4,4'-bis(1,2,2,6,6-pentamethyl-4-piperidyl)biphenyl, poly-N,N'-bis-(2,2,6,6-tetramethyl-4-piperidyl)-1,8-diazadecylene, adduct of 2,2,6,6-tetramethyl-4-allyloxypiperidine and polymethylhydrosiloxane (molar mass up to 4000), adduct of 1,2,2,6,6-pentamethyl-4-allyloxypiperidine and polymethylhydrosiloxane (molar mass up to 4000), N,N'-diformyl-N,N'-bis(2,2,6,6-tetramethyl-4-piperidinyl)hexamethylenediamine, N,N'-diformyl-N,N'-bis(1,2,2,6,6-pentamethyl-4-piperidinyl)hexamethylenediamine, 5,11-bis(2,2,6,6-tetramethyl-4-piperidinyl)-3,5,7,9,11,13-hexaazatetracyclo-[7.4.0.0$^{2,7}$.1$^{3,13}$]tetradecane-8,14-dione, 5,11-bis(1,2,2,6,6-pentamethyl-4-piperidinyl)-3,5,7,9,11,13-hexaazatetracyclo[7.4.0.0$^{2,7}$.1$^{3,13}$]tetradecane-8,14-dione, [(4-methoxyphenyl)methylene]-propanedioic acid bis(2,2,6,6-tetramethyl-4-piperidinyl)ester, [(4-methoxyphenyl)-methylene]propanedioic acid bis(1,2,2,6,6-pentamethyl-4-piperidinyl)ester, 2,4,6-tris(N-cyclohexyl-N-[2-(3,3,4,5,5-pentamethylpiperazinon-1-yl)ethyl]amino)-1,3,5-triazine, copolymer of styrene with α-methylstyrene and maleic anhydride reacted with 4-amino-2,2,6,6-tetramethylpiperidine and octadecylamine, copolymer of styrene with α-methylstyrene and maleic anhydride reacted with 4-amino-1,2,2,6,6-pentamethylpiperidine and octadecylamine, polycarbonate with 2,2'-[(2,2,6,6-tetramethyl-4-piperidinyl)imino]bis[ethanol] as diol component, polycarbonate comprising 2,2'-(1,2,2,6,6-pentamethyl-4-piperidinyl)imino]bis[ethanol] as diol component, copolymer of maleic anhydride and an α-olefin up to $C_{30}$ reacted with 4-amino-2,2,6,6-tetramethylpiperidine, copolymer of maleic anhydride and an α-olefin up to $C_{30}$ reacted with 1-acetyl-4-amino-2,2,6,6-tetramethylpiperidine, copolymer of maleic anhydride and an α-olefin up to $C_{30}$ reacted with 4-amino-1,2,2,6,6-pentamethylpiperidine, and also the N-alkyl- and N-aryl-oxy derivatives of the abovementioned compounds with free NH groups on the piperidine, especially α-methylbenzyloxy and alkyloxy from $C_1$ to $C_{18}$.

2.7 Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted and of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4',6-bis(2',4'-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[hydroxy-4-(2-hydroxy-3-octyloxypropyloxy)phenyl]-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[4-dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine.

3. Metal deactivators, for example, N,N'-diphenyloxalamide, N-salicylal-N'salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tertbutylphenyl) phosphite, diisodecyl pentaerythritol diphosphite, bis(2,4-di-tertbutylphenyl) pentaerythritol diphosphite, bis(2,6-di-tert-butyl-4-methylphenyl) pentaerythritol diphosphite, bisisodecyloxy pentaerythritol diphosphite, bis(2,4-di-tert-butyl-6-methylphenyl)pentaerythritol diphosphite, bis(2,4,6-tri-tert-butylphenyl) pentaerythritol diphosphite, tristearyl sorbitol triphosphite, tetrakis(2,4-di-tert-butylphenyl) 4,4'-biphenylenediphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl) methyl phosphite, bis(2,4-di-tert-butyl-6-methylphenyl)ethyl phosphite, tris(2-tert-butyl-4-thio(2'-methenyl-4'-hydroxy-5'-tert-butyl)phenyl-5-methenyl) phenyl phosphite, 2,2',2''-nitrilo[triethyl tris(3,3',5,5'-tetra-tert-butyl-1,1'-biphenyl-2,2'-diyl)phosphite], bis[2-methyl-4,6-bis(1,1-dimethylethyl)phenol]phosphorous acid ethyl ester.

5. Hydroxylamines, examples being N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamines prepared from hydrogenated tallow fatty amine.

6. Nitrones, examples being N-benzyl alpha-phenyl nitrone, N-ethyl alpha-methyl nitrone, N-octyl alpha-heptyl nitrone, N-lauryl alpha-undecyl nitrone, N-tetradecyl alpha-tridecyl nitrone, N-hexadecyl alpha-pentadecyl nitrone, N-octadecyl alpha-heptadecyl nitrone, N-hexadecyl alpha-heptadecyl nitrone, N-octadecyl alpha-pentadecyl nitrone, N-heptadecyl alpha-heptadecyl nitrone, N-octadecyl alpha-hexadecyl nitrone, nitrones derived from N,N-dialkylhydroxylamines prepared from hydrogenated tallow fatty amines.

7. Zeolites and hydrotalcites, such as DH® 4A from Kisuma, Hycithe® 713 from Südchemie or Pural® MG 61 HT from Condea.

Hydrotalcites of this kind can be described by the formula $$[(M^{2+})_{1-x}(M^{3+})_x(OH)_2(A^{n-})_{x/n}yH_2O],$$

where $(M^{2+})$ is Mg, Ca, Sr, Ba, Zn, Pb, Sn, Ni
$(M^{3+})$ is Al, B, Bi
$A^n$ is an anion of valency n
n is an integer from 1-4
x is a value between 0 and 0.5
y is a value between 0 and 2
A is $OH^-$, $Cl^-$, $Br^-$, $I^-$, $ClO_4^-$, $CH_3COO^-$, $C_6H_5COO^-$ $CO_3^{2-}$, $SO_4^{2-}$, $(OOC—COO)^{2-}$ $(CHOHCOO)_2^{2-}$, $(CHOH)_4CH_2OHCOO^-$, $C_2H_4(COO)_2^{2-}$, $(CH_2COO)_2^{2-}$, $CH_3CHOHCOO^-$, $SiO_3^{2-}$, $SiO_4^{4-}$, $Fe(CN)_6^{3-}$, $Fe(CN)_6^{4-}$, $BO_3^{3-}$, $PO_3^{3-}$, $HPO_4^{2-}$.

Preference is given to employing hydrotalcites in which $(M^{2+})$ is $(Ca^{2+})$, $(Mg^{2+})$ or a mixture of $(Mg^{2+})$ and $(Zn^{2+})$; $(A^{n-})$ is $CO_3^{2-}$, $BO_3^{3-}$, $PO_3^{3-}$; x has a value from 0 to 0.5 and y has a value from 0 to 2. It is also possible to employ hydrotalcites that can be described with the formula $$[(M^{2+})_x(Al^{3+})_2(OH)_{2x+6nz}(A^{n-})_2yH_2O]$$

Here, $(M^{2+})$ is $Mg^{2+}$, $Zn^{2+}$, but more preferably $Mg^{2+}$. $(A^{n-})$ is an anion, in particular from the group consisting of $CO_3^{2-}$, $(OOC—COO)^{2-}$, $OH^-$ and $S^{2-}$, where n describes the valency of the ion. y is a positive number, more preferably between 0 and 5, especially between 0.5 and 5. x and z have positive values, which in the case of x are preferably between 2 and 6 and in the case of z should be less than 2. The hydrotalcites of the following formulae are to be regarded with particular preference:

$$Al_2O_3 \times 6MgO \times CO_2 \times 12H_2O,$$

$$Mg_{4.5}Al_2(OH)_{13} \times CO_3 \times 3.5H_2O,$$

$4MgO \times Al_2O_3 \times CO_2 \times 9H_2O$, $4MgO \times Al_2O_3 \times CO_2 \times 6H_2O$, $ZnO \times 3MgO \times Al_2O_3 \times CO_2 \times 8\text{-}9H_2O$, $ZnO \times 3MgO \times Al_2O_3 \times CO_2 \times 5\text{-}6H_2O$, $Mg_{4.5}Al_2(OH)_{13} \times CO_3$.

Hydrotalcites are employed in the polymer preferably in a concentration of from 0.01 to 5% by weight, in particular from 0.2 to 3% by weight, based on the overall polymer formulation.

8. Thiosynergists, examples being dilauryl thiodipropionate and distearyl thiodipropionate.
9. Peroxide scavengers, examples being esters of β-thiodipropionic acid, for example the lauryl, stearyl, myristyl or tridecyl ester, mercaptobenzimidazole, the zinc salt of 2-mercaptobenzimidazole, zinc alkyldithiocarbamates, zinc dibutyldithiocarbamate, dioctadecyl monosulphide, dioctadecyl disulphide, pentaerythritol tetrakis(β-dodecylmercapto)propionate.
10. Polyamide stabilizers, examples being copper salts in combination with iodides and/or phosphorus compounds and salts of divalent manganese.
11. Basic costabilizers, examples being melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg behenate, Mg stearate, Na ricinoleate, K palmitate, antimony pyrocatecholate or tin pyrocatecholate.
12. Nucleating agents, such as inorganic substances, examples being talc, metal oxides, such as titanium dioxide or magnesium oxide, phosphates, carbonates or sulphates of, preferably, alkaline earth metals, organic compounds, such as mono- or polycarboxylic acids and also their salts, examples being 4-tert-butylbenzoic acid, adipic acid; diphenylacetic acid; sodium succinate or sodium benzoate; acetals of aromatic aldehydes and polyfunctional alcohols such as sorbitol, for example, such as 1,3-2,4-di(benzylidene)-D-sorbitol, 1,3-2,4-di(4-tolylidene)-D-sorbitol, 1,3-2,4-di(4-ethylbenzylidene)-D-sorbitol, polymeric compounds, such as ionic copolymers (ionomers), for example.
13. Fillers and reinforcing agents, examples being calcium carbonate, silicates, glass fibres, asbestos, talc, kaolin, mica, barium sulphate, metal oxides and metal hydroxides, carbon black, graphite, wood flour and other flours or fibres of other natural products, synthetic fibres.
14. Other additives, examples being plasticizers, lubricants, emulsifiers, pigments, rheological additives, catalysts, levelling assistants, optical brighteners, flame retardants, antistatics, blowing agents.
15. Benzofuranones and indolines, as described, for example, in U.S. Pat. No. 4,325,863, U.S. Pat. No. 4,338,244, U.S. Pat. No. 5,175,312; U.S. Pat. No. 5,216,052; U.S. Pat. No. 5,252,643, DE-A-4316611, DE-A-4316622, DE-A-4316876, EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuranon-2-one, 3,3'-bis [5,7-di-tert-butyl-3-(4-[2-hydroxyethoxy]phenyl) benzofuran-2-one, 5,7-di-tert-butyl-3-(4-ethoxyphenyl) benzofuran-2-one, 3-(4-acetoxy-3,5-dimethylphenyl)-5, 7-di-tert-butylbenzofuran-2-one, 3-(3,5-diethyl-4-pivaloyloxyphenyl)-5,7-di-tert-butylbenzofuran-2-one.

The various addition additives from groups 1 to 12 and group 15 above are added to the polymers to be stabilized in an amount of from 0.01 to 10%, preferably from 0.01 to 5%, by weight based on the overall weight of the organic material to be stabilized. The proportion of the additives from groups 13 and 14 is from 0.1 to 80% by weight, preferably from 0.1 to 50% by weight, based on the organic material to be stabilized.

The additives are incorporated into the organic material to be stabilized, using usual and well-known methods. For example, incorporation may take place by mixing in or applying the mixture of the invention and, if desired, further additives into or to the polymer immediately following polymerization or in the melt prior to or during shaping.

Incorporation may also take place by applying the dissolved or dispersed compounds to the polymer directly or by mixing them into a solution, suspension or emulsion of the polymer, where appropriate with subsequent evaporation of the solvent.

The compounds are also effective if incorporated subsequently, in a separate processing step, into a polymer which has already been granulated.

The compounds prepared in accordance with the invention may also be added in the form of a masterbatch, containing these compounds, for example, in a concentration of from 1 to 75% by weight, preferably from 2.5 to 60% by weight, to the polymers that are to be stabilized.

The process of the invention affords the critical advantage that mixtures of components (I), (II) and (III) can be prepared not by time-consuming, complicated and costly mixing of the individually prepared components but instead, advantageously and surprisingly, by a clever reaction regime in situ.

The examples which follow serve to illustrate the subject-matter of the invention:

EXAMPLES 1-6

For the values of the stated variables x and y, see Table 1.

x g of xylene were admixed in succession with 200.3 g (0.50 mol) of 2,2,4,4-tetramethyl-7-oxa-3,20-diaza-21-oxo-dispiro[5.1.11.2]heneicosane hydrochloride, 10 g of polyethylene glycol 200 and y g of epichlorohydrin and 164.0 g of 50% strength aqueous sodium hydroxide solution (2.05 mol).

This mixture was stirred at 70° C. for 40 minutes. After the excess epichlorohydrin and the xylene solvent had been distilled off, 220 g of xylene and 220 g of water were added to the reaction mixture and the phases were separated. The organic phase was washed twice with 110 g of water each time. Distillative removal of the solvent under reduced pressure gave a yellowish oil which was reacted without further purification at 200° C. under full vacuum to give the desired mixture. The product is a brittle, almost colourless resin, whose yield, melting range and solution viscosity are summarized in Table 1.

TABLE 1

| Example No. | x (g) (Xylene) | y (g) (epichlorohydrin) | Yield (g) | Melting range (° C.) | Solution viscosity (mm$^2$/s)[1] |
|---|---|---|---|---|---|
| 1 | 345.0 | 115.6 | 98.5 | 158-210 | 1.83 |
| 2 | 114.9 | 115.6 | 98.1 | 166-216 | 2.23 |
| 3 | 172.5 | 115.6 | 98.2 | 163-216 | 2.09 |
| 4 | 241.5 | 115.6 | 98.7 | 160-210 | 2.00 |
| 5 | 345.0 | 92.5 | 96.0 | 153-202 | 1.64 |
| 6 | 345.0 | 104.1 | 99.0 | 146-197 | 1.75 |

[1] 20% strength solution in toluene at 25° C. in accordance with DIN 51562

Examples 1, 5 and 6 are comparative examples.

The invention claimed is:

1. A process for preparing a synergistic stabilizer mixture comprising the components of the general formulae (I), (II) and (III), wherein the mixture comprises compound (I) in a fraction of 65-95%, compound, by weight (II) in a fraction of from 5 to 35%, by weight, and compound (III) in a fraction of from 0 to 10% by weight,

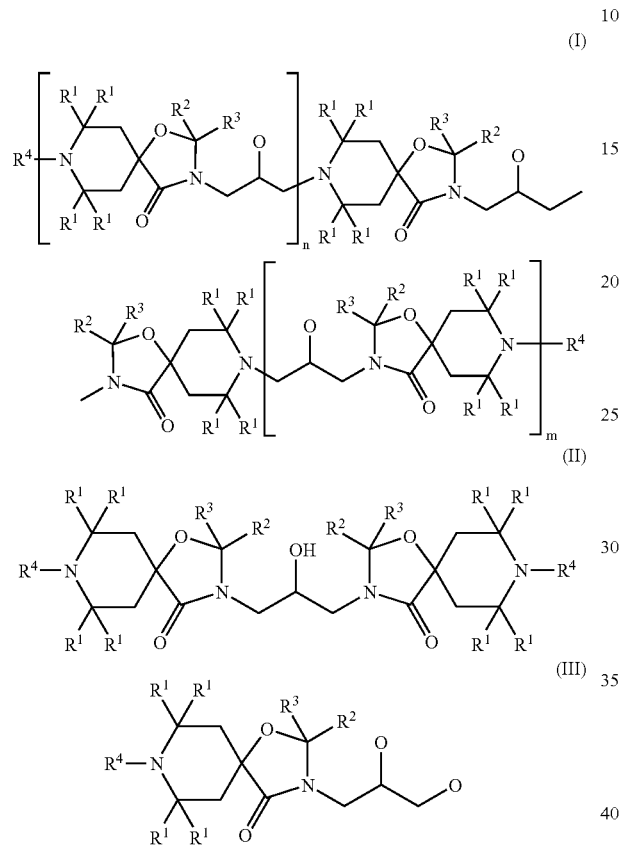

wherein
n and m independently of one another are a number from 0 to 100, but cannot both be 0,
$R^1$ is hydrogen, $C_5$-$C_7$ cycloalkyl or a $C_1$-$C_{12}$ alkyl group,
$R_2$ and $R_3$ independently of one another are a hydrogen atom, a $C_1$-$C_{18}$ alkyl group or, together with the carbon atom connecting them, a ring with a size of from 5 to 13 or, together with the carbon atom joining them, a group of the formula (IV),

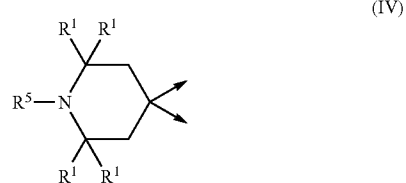

$R^4$ and $R^6$ independently of one another are either hydrogen, a $C_1$-$C_{22}$ alkyl group, an oxygen radical O*, —OH, —NO, —CH$_2$CN, benzyl, allyl, a $C_1$-$C_{30}$ alkyloxy group, a $C_5$-$C_{12}$ cycloalkyloxy group, a $C_6$-$C_{10}$ aryloxy group, in which the aryl radical may optionally be substituted further, a $C_7$-$C_{20}$ arylalkyloxy group, in which the aryl radical may optionally be substituted further, a $C_3$-$C_{10}$ alkenyl group, a $C_3$-$C_8$ alkynyl group, a $C_1$-$C_{10}$ acyl group, halogen, unsubstituted phenyl or $C_1$-$C_4$ alkyl-substituted phenyl, comprising the steps of reacting at least one compound of the formula (V)

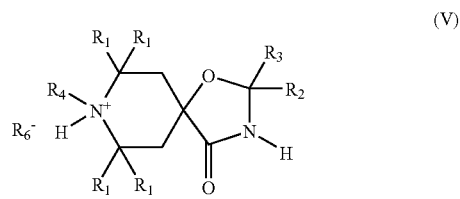

in which $R^1$, $R^2$, $R^3$ and $R^4$ are as defined above and $R_6^-$ is the anion of a protic acid
with an epihalohydrin of the formula (VI)

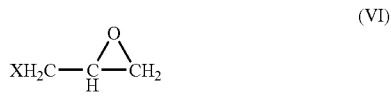

in which X is a chlorine, bromine or iodine atom
and in an inert organic solvent in a phase transfer reaction to form a reaction mixture, and polymerizing the reaction mixture,
wherein the inert organic solvent is used in a ratio of from 2:1 to 1:5 with respect to compound (VI).

2. The process according to claim 1, further comprising the steps of premixing the compounds (V), (VI) and a phase transfer catalyst in the inert organic solvent, and adding from 4 to 20 times the molar amount, relative to compound (V), of a solid alkali metal hydroxide or of an aqueous solution of an alkali metal hydroxide, prior to the reacting step, wherein the reacting step occurs at a temperature of from 20 to 220° C., wherein the reacting step further comprises removing the excess epihalo-hydrin (VI), separating off the organic phase and removing the inert organic solvent prior to the polymerization step, and wherein the polymerization step further comprises polymerizing the organic phase at a temperature of from 100 to 240° C.

3. The process according to claim 2, wherein the compounds (V) and (VI) are premixed in a molar ratio of from 1:1 to 1:2.9.

4. The process according to claim 2, wherein the phase transfer catalyst is a polyethylene glycol.

5. The process according to claim 1, wherein the inert organic solvent is xylene.

6. The process according to claim 1, wherein the inert organic solvent is used in a ratio of from 2:1 to 1:3, with respect to compound (VI).

7. The process according to claim 1, wherein the inert organic solvent is used in a ratio of from 2:1 to 1:2, with respect to compound (VI).

8. The process according to claim 2, wherein the alkali metal hydroxide is sodium hydroxide in solid form or in aqueous solution.

9. The process according to claim 1, wherein in the aqueous solution the ratio of alkali metal hydroxide to water is in the range from 9:1 to 1:9.

10. The process according to claim 9, wherein in the aqueous solution the ratio of alkali metal hydroxide to water is from 2:3 to 4:1.

11. The process according to claim 1, wherein the reaction takes place at a temperature of from 40 to 120° C.

12. The process according to claim 1, further comprising removing excess epihalohydrin (VI) and the inert organic solvent by distillation.

13. The process according to claim 1, wherein polymerization takes place at a temperature of from 120 to 220° C.

14. The process according to claim 1, wherein polymerization takes place under reduced pressure.

15. The process according to claim 1, wherein the compound of the formula (V) is 2,2,4,4-tetramethyl-7-oxa-3,20-diaza-21-oxodispiro[5.1.11.2]heneicosane hydrochloride.

16. The process according to claim 1, wherein the compound of the formula (VI) is epichlorohydrin.

17. A masterbatch comprising at least one organic material and a synergistic stabilizer mixture made in accordance with claim 1, wherein the synergistic stabilizer mixture is present at a concentration of from 2,5 to 60% by weight relative to the organic material.

18. The process according to claim 9, wherein in the aqueous solution the ratio of alkali metal hydroxide to water is from 1:1 to 7:3.

19. The process according to claim 1, wherein the reaction takes place at a temperature of from 60 to 90° C.

20. The process according to claim 1, wherein polymerization takes place at a temperature of from 150 to 200° C.

21. The process according to claim 1, wherein the mixture comprises compound (I) in a fraction of from 75 to 94% by weight.

22. The process according to claim 1 wherein the mixture comprises compound (I) in a fraction of from 85 to 94% by weight.

23. The process according to claim 1, wherein the mixture comprises compound (II) in a fraction of from 5 to 20% by weight.

24. The process according to claim 1, wherein the mixture comprises compound (II) in a fraction of from 5 to 12% by weight.

25. The process according to claim 1, wherein the mixture comprises compound (III) in a fraction of from 1 to 5% by weight.

26. The process according to claim 1, wherein the mixture comprises compound (III) in a fraction of from 1 to 3% by weight.

27. The process according to claim 2, wherein the compounds (V) and (VI) are premixed in a molar ratio of from 1:2 to 1:2.5.

28. A synergistic stabilizer mixture made in accordance with the process of claim 1.

29. An organic material comprising the synergistic stabilizer mixture of claim 28.

30. The organic material according to claim 29 further comprising at least one compound selected from the group consisting of antioxidants, light stabilizers, metal deactivators, antistatic agents, flame retardants, lubricants, nucleating agents, acid scavengers, pigments and fillets.

31. A masterbatch composition comprising the synergistic stabilizer mixture of claim 28.

* * * * *